United States Patent [19]
Wikström

[11] Patent Number: 5,981,164
[45] Date of Patent: *Nov. 9, 1999

[54] METHOD FOR DETECTING *PORPHYROMONAS GINGIVALIS*

[76] Inventor: Maude Birgitta Wikström, Trolldansen 8, Mölndal, Sweden, S-431 69

[ * ] Notice: This patent issued on a continued prosecution application filed under 37 CFR 1.53(d), and is subject to the twenty year patent term provisions of 35 U.S.C. 154(a)(2).

[21] Appl. No.: 08/371,479

[22] Filed: Jan. 11, 1995

Related U.S. Application Data

[63] Continuation of application No. 08/041,295, Mar. 29, 1993, abandoned, which is a continuation of application No. 07/597,817, Oct. 15, 1990, abandoned.

[51] Int. Cl.$^6$ .............................. C12Q 1/00; C12N 9/48
[52] U.S. Cl. .............................. 435/4; 435/212; 435/810; 435/822
[58] Field of Search .................................. 435/23, 24, 29, 435/34, 822, 810, 4

[56] References Cited

FOREIGN PATENT DOCUMENTS

| | | | |
|---|---|---|---|
| 0255341 | 2/1988 | European Pat. Off. | C12Q 1/36 |
| 0292708 | 4/1988 | European Pat. Off. | C12Q 1/04 |
| 0292708 | 11/1988 | European Pat. Off. | C12Q 1/04 |
| 0325472 | 7/1989 | European Pat. Off. | |

OTHER PUBLICATIONS

Z. Chen et al., "Stimulation of Proteinase and Amidase Activities in Porphyromonas (Bacteroides) gingivalis by Amino Acids and Dipepties," Infection and Immunity, vol. 59, No. 8, pp. 2846–2850, Jul. 1991.
Frankfater A. et al.; Biochemistry 1981, vol. 20, pp. 5517–5524.
Loeche W.J. et al.; *J. Periodontolgy*; 1990; vol. 61; No. 3; pp. 189–196.
Bajkowski A.S. et al.; *The Journal of Biologic Chemistry*; 1983, vol. 258; No. 3; pp. 1645–1549, 1650–1655.
Chemical Abstracts, vol. 108, No. 7, Abstract No. 53708s.
Bretz, et al., *J. Dent. Res.*, vol. 66, No. 11, 1987, pp. 1668–1672.
Ono, et al., *Oral Microbiol. Immunol.*, 1987: 2:77–81.

*Primary Examiner*—Bradley L. Sisson
*Attorney, Agent, or Firm*—Fulbright & Jaworski L.L.P.

[57] ABSTRACT

A rapid and simple method and kit for the analysis of *Porphyromonas gingivalis* in a sample. A sample suspected of containing *P. gingivalis* is assayed for enhanced proteolytic, amidolytic, or esterolytic activity in the presence of a specific enhancer compound. Specifically, the enhancer is a mono- or di-peptide containing glycine, or an amide or ester thereof.

32 Claims, 6 Drawing Sheets

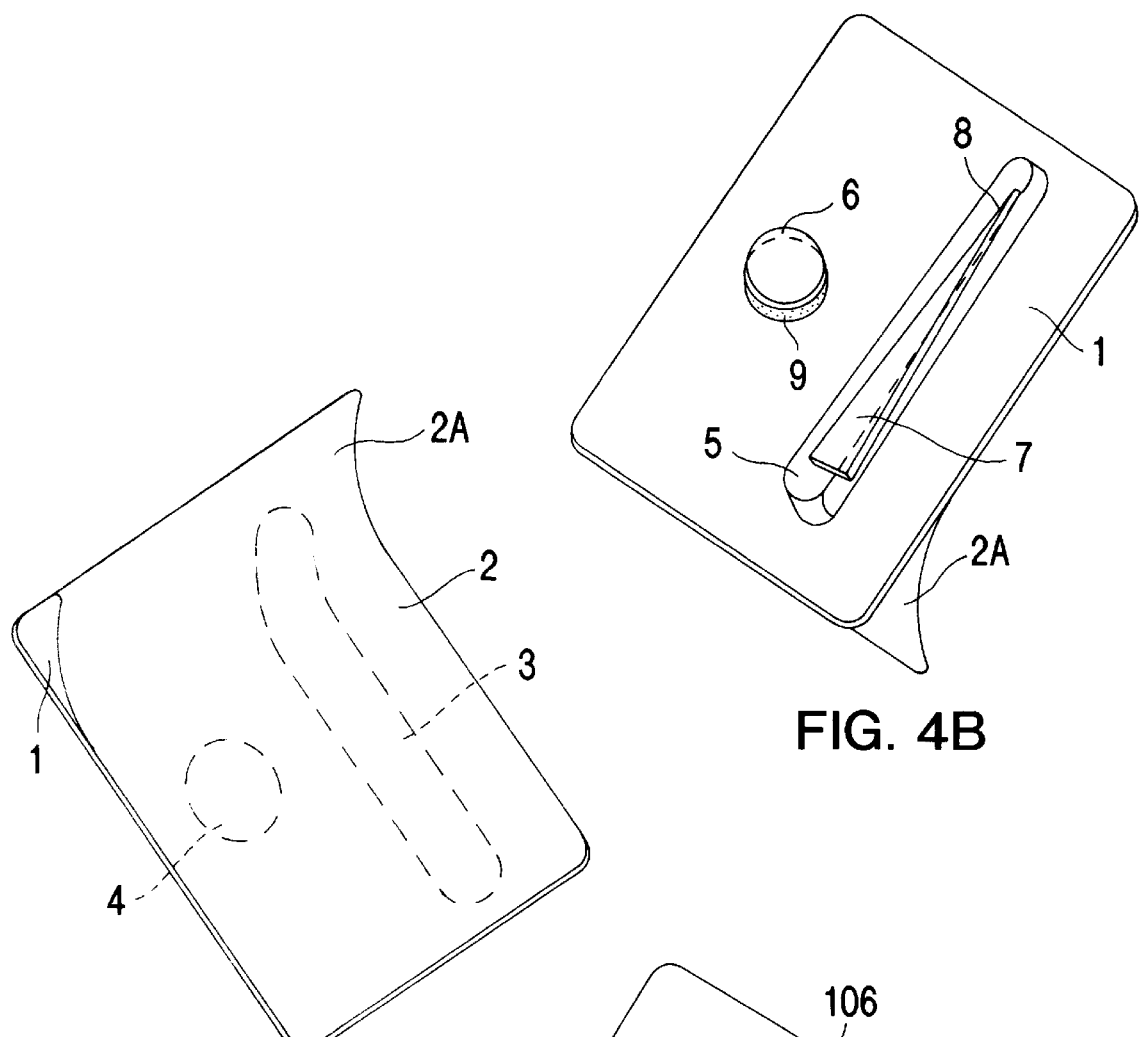
FIG. 4A
FIG. 4B
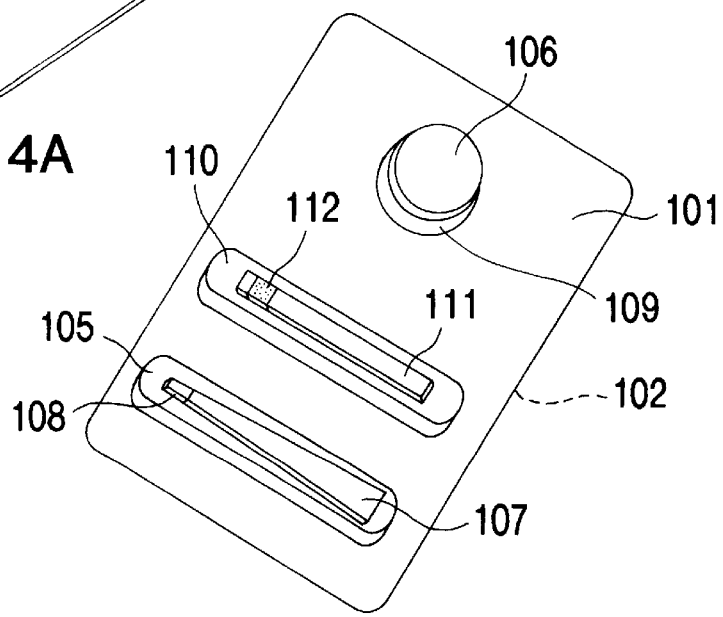
FIG. 4C

METHOD FOR DETECTING *PORPHYROMONAS GINGIVALIS*

This application is a continuation of U.S. application Ser. No. 08/041,295 filed on Mar. 29, 1993, now abandoned, which is a continuation of U.S. application Ser. No. 07/597,817 filed Oct. 15, 1990 now abandoned.

The present invention is related to a method of determining proteolytic activity of an enzyme from *Porphyromonas gingivalis* formerly named *Bacteroides gingivalis*, below referred to as *P. gingivalis*. An object of the invention is to facilitate and/or reduce the cost of qualitative and quantitative determination of *P. gingivalis* in diagnosis of *periodontitis* and/or in laboratory techniques where proteolytic enzymes from *P. gingivalis* occur, especially where such enzymes occur in very small amounts.

BACKGROUND

According to recent data, almost all adults show clinical signs of inflammation in the gums, gingivitis, at one or more tooth sites. About 11% of the population shows pronounced destruction of the tooth supporting tissues, i.e. *periodontitis*. The clinical signs of inflammation are redness, bleeding on probing and suppuration. However, these clinical parameters are not reliable predictors of tissue destruction.

Most, if not all forms, of periodontal diseases are caused by bacteria. Recent clinical and microbial investigations have revealed that specific gram negative bacteria play an ethological role in different forms of human periodontal diseases. *Porphyromonas gingivalis* has been associated with progressive adult *periodontitis*. Thus, the presence of *P. gingivalis* could be used as a guideline for selection of treatment regime and for treatment evaluation. Identification of *P. gingivalis* is commonly performed using cultivation techniques. Microbial sampling and culturing is usually performed as in the following example:

Sterile paperpoints are inserted into the periodontal pocket and left in place for 15 s. The points are pooled in a vial containing glass beads and transport medium. At the microbial laboratory, the samples are thoroughly desintegrated and diluted. A volume of 0.1 ml from each dilution as well as from the undiluted sample is distributed on the surface of *Brucella agar* plates (BBL Microbiology Systems, Cockeysville, Md., USA) enriched with 5% defibrinated horse blood, 0.5% haemolyzed blood and 5 mg/l of menadion. After 7–9 days of incubation, in jars with 95% $H_2$ and 5% $CO_2$, total viable count and the number of *P. gingivalis* colonies in the sample is determined. The *P. gingivalis* colonies are identified by gram staining, lactose fermentation test, and checking for production of red fluorescence in long-wave (360 nm) UV-light. The handling of the sample is time consuming and personal intensive and therefore expensive. Also it will take about 2 weeks before the therapist can have the result of the test.

Today about 3000 microbial samples are sent for analysis to the Dept of Oral Microbiology in Göteborg. This laboratory is one of the 4 Oral Microbiology Departments in Sweden to which samples could be sent for analysis. The cost for the analysis of 1 sample is 150 SEK, which limits the number of samples taken from each patient. *P. gingivalis* is known to produce high proteolytic activity which can a) destroy in vitro many components of connective tissue and b) degrade other proteins important for the maintaining of local homeostasis e.g. the inactivating of inhibitors controlling host proteinases.

EP-A2 0 255 341 (Sunstar Kabushiki Kaisha) discloses a periodontal diagnosis reagent, which comprises peptide(s) having attached thereto a colour developing group for detecting aminopeptidase-like enzymatic activity in an oral sample. EP-A2 0 292 708 (The Research Foundation of State University of New York) relates to detection of *Bacteroides gingivalis* using a serum aminopeptidase inhibitor in an assay system, and measuring the ability to hydrolyse N-carbobenzoxy-glycyl-glycyl-L-arginine-β-naphtylamide derivatives. Use of enhancers of the enzymatic activity of *Bacteroides gingivalis* such as chelating materials, specifically tetrasodium ethylene-diaminetetraacetate (EDTA) is proposed.

DISCLOSURE OF THE INVENTION

The present invention relates to a method of determining *P. gingivalis* in diagnosis and/or treatment of *periodontitis*, whereby a sample is taken from a possible site of *P. gingivalis* and said sample is added to a composition comprising a substrate subject to protcolysis, amidolysis or proteolysis and at least one activator for the proteolytic, amidolytic or esterolytic activity of one or more enzymes from *P. gingivalis* on said substrate; said activator being cysteine, cysteamine, glycine, or a di- or tripeptide containing glycine, or an amide or a lower alkyl ester of glycine or such di- or tripeptide, or a decarboxylated derivative of such di- or tripeptide, and determining proteolytic, amidolytic or esterolytic activity from said sample in said composition.

According to a further aspect, the invention relates to a kit for determining of *Porphyromonas gingivalis* (*P. gingivalis*, formerly *Bacteroides gingivalis*) in diagnosis and/or treatment of *periodontitis* comprising a sampling device for collection of a sample from a possible site of *P. gingivalis*, said kit further comprising a composition comprising a substrate subject to proteolysis, amidolysis or esterolysis, and at least one activator for the proteolytic, amidolytic or esterolytic activity of one or more enzymes from *P. gingivalis* on said substrate; said activator being cysteine, cysteamine, glycinc, or a di- or tripeptide containing glycine, or an amide or a lower alkyl ester of glycine or such di- or tripeptide, or a decarboxylated derivative of such di- or tripeptide.

Preferred substrates for use according to the invention are D- or L-amino acids or peptides of 2–6 D- or L-amino acids having arginine at the P1 position, to which a chromogenic or fluoroqenic group is attached by an amide or an ester bond, e.g. such substrates disclosed in EP-A2-0 255 341, such as glycyl-arginine-β-naphtylamide, arginyl-arginine-β-naphtylamide, lysyl-arginine-β-naphtylamide, phenylalanyl-arginine-β-naphtylamide, prolyl-phonylalanyl-arginine-β-naphtylamide, N-benzoy-glycyl-arginine-β-naphtylamide, N-carboxybenzoxy-arginyl-arginine-β-naphtylamide, N-carboxybenzoxy-phenylalanyl-arginine-β-naphtylamide, N-carboxybenzoxy-lysyl-arginine-β-naphtylamide, N-carboxybenzoxy-valyl-glycyl-arginine-β-naphtylamide, N-benzoyl-valyl-glycyl-arginine-β-naphtylamide, N-t-butoxycarbonyl-valyl-lcucyl-glycyl-arginine-β-naphtylamide, N-succinyl-glycyl-prolyl-loucyl-glycyl-arginine-β-naphtylamide.

Preferably the activator is other than glycine since its protcolysis-activating effect is comparatively low. Similarly, cysteamine is non-preferred as sole activator, since it requires a concentration of at least 200 mM for sufficient effect. However reducing agents such as cysteamine and mercaptoethanol are preferably used along with one of the activators (other than cysteamine).

In di- and tripeptides, their amides and esters, as activators, glycine may be in either position and may occur once or twice, and three times (in glycyl-glycyl-glycine, its amides and esters). Preferably a sole glycine, or an acidic amino acid such as aspartic or glutamic acid, is however not the C-terminal amino acid in the di- and tri-peptides with unblocked carboxyl group.

In the peptide activators, their amides and esters, the amino acids in addition to glycine are selected from naturally occurring α-amino acids and their D-analogues. According to an embodiment of the invention the amide of glycine or the di- or tripeptide is

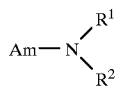

wherein Am is the residue of glycine, di- or tri-peptide and $R^1$ and $R^2$ are each selected from H, or an aliphatic, heteroaliphatic, aromatic or heteroaromatic group containing 1–9 carbon atoms. Preferably $R^1$ and $R^2$ are each selected from H, or an aliphatic, aromatic or hetero-aromatic group containing 1–4 most preferably 1–3 carbon atoms.

According to an embodiment of the invention $R^1$ and $R^2$ are each selected from H or an alkyl or alkenyl group having 1–3 carbon atoms.

According to an embodiment of the invention $R^1$ and $R^2$ are each selected from H or an phenyl, 2-, 3-, 4-pyridyl or a 9-anthacene group.

Preferably $R^2$ is H and most preferably $R^1$ and $R^2$ are both H.

According to an embodiment of the invention the ester is Am-$OR^3$ wherein Am is the residue of glycine, di- or tripeptide peptide and $R^3$ is an alkyl or alkenyl group containing 1–5 carbon atoms.

The best embodiment of the invention known to the inventor is employing Gly-$NH_2$ and cysteamine in a buffer, in a device as shown below in FIG. 4A. The concentration of activator in the composition employed by the invention is suitably 10 to 200 mM preferably 20 to 100 mM.

DRAWINGS

In the appended drawings,

FIG. 4A is a view from the above side of a diagnostic test kit according to one specific embodiment of the invention, while FIG. 4B is a view of the kit in FIG. 4 shown from the below side thereof, and FIG. 4C is a sketch view from above of a diagnostic test kit according to another specific embodiment of the invention.

Figure 1:
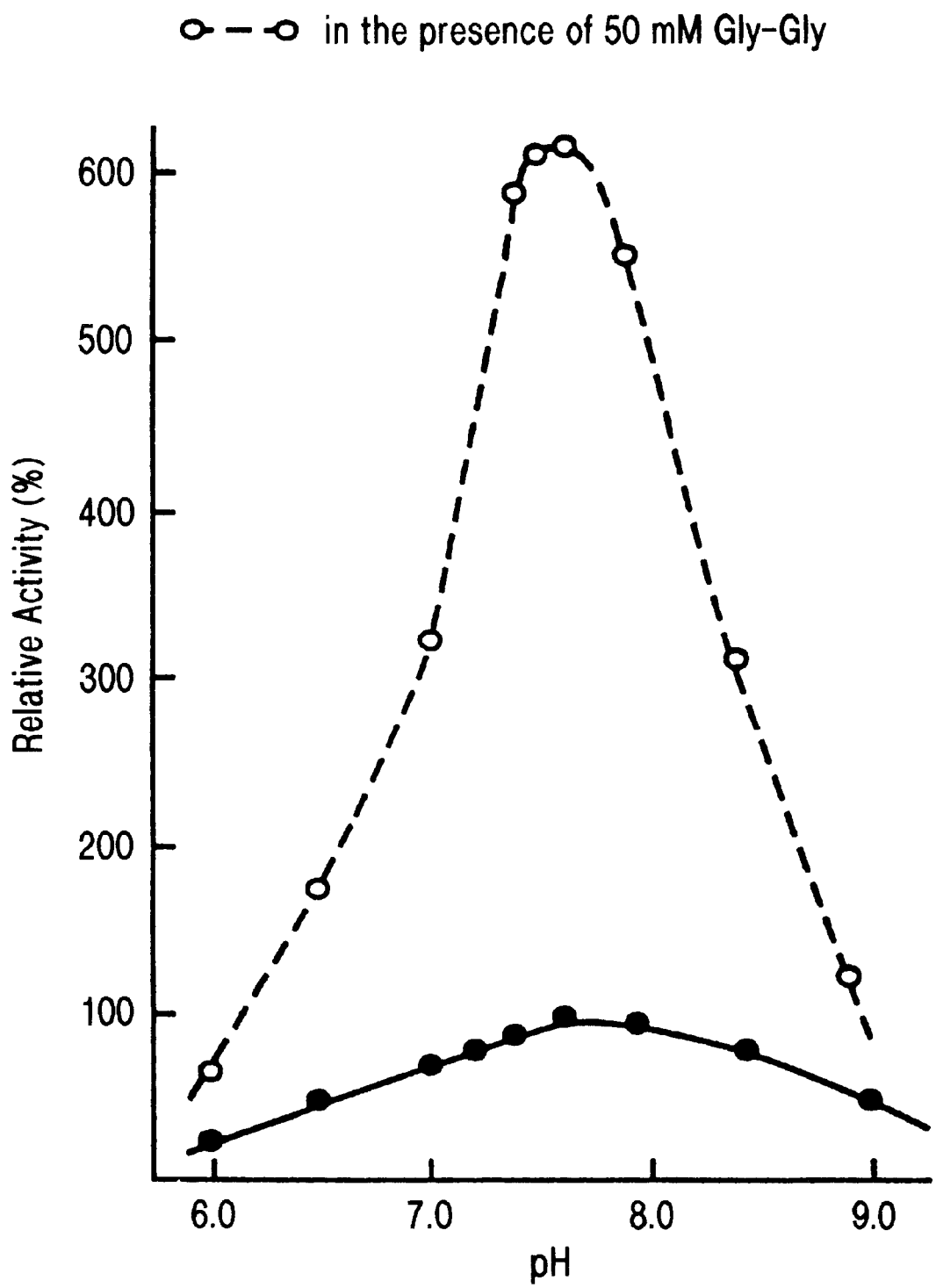
FIG. 1 is a diagram showing pH dependent activity of *P. gingivalis* crude extracts.

In FIGS. 4A and B, 1 is a blister card made of rigid blister material having securely and leak-free but releasably attached thereto a plastic-coated aluminium foil cover 2, having a released end portion 2A. Hinted at 3 is a portion of 2 covering a sampling stick blister 5 and hinted at 4 is a portion of 2 covering a blister 6 for holding a liquid or jelly composition. Items 5 and 6 are vacuum formed from 1. Item 7 Is a sampling stick having a point 8 on which a sample may be adsorbed, Denoted 9 is a liquid or jelly buffer solution containing a substrate for *P. gingivalis* enzyme and an activator, said substrate having a chromogenic leaving group.

Use of the device in FIGS. 4A and B is generally as follows. Placing 1 horizontally as in FIG. 4A, 2 is removed. 7 is taken by the broad end and a sample is taken at 8. 8 is immersed in 9. A color change in 9 indicates presence at the sampling site of *P. gingivalis*.

In another embodiment the device of FIGS. 4A and 4B may be varied by incorporating a second blister holding a liquid or jelly buffer solution containing the same substrate without activator, and a second blister holding a second sampling stick. Said second solution and sampling stick serve for control of amidolytic activity unrelated to *P. gingivalis*.

The device in FIG. 4C is similar to that in FIGS. 4A and B, and items 101 through 108, when shown, generally correspond to items 1 through 8, except that 109 does not contain a substrate with a chromogenic group. Instead, said substrate is placed on a distal portion 112 of a test strip 111 in a test strip blister 110. After sampling with 107. 108 is immersed in 109 to allow the sample to dissolve or suspend in liquid 109. Test strip 111 is taken from the end opposite to 112, and 112 is immersed in 109. A color change on 112 indicates presence at the sampling site of *P. gingivalia*.

In another embodiment the device of FIG. 4C may be varied by incorporating a second blister holding a second test strip impregnated with the same substrate without activator. Said second test strip serves for control of amidolytic activity unrelated to *P. gingivalis*.

EXPERIMENTAL

In order to understand the physiological mechanism(s) by which *P. gingivalis* functions in tissue destruction a detailed study was made of the properties of the major proteinases in this organism, the majority of which are trypsin-like in nature. During their isolation it was found that these activities were substantially stimulated by glycine-containing compounds, including dipeptides and glycine derivatives, a property not heretofore previously noted for proteinases. In this application is described the effect of such compounds on both the amidase and caseinolytic activity of *P. gingivalis* extracts and two enzymes purified from this organism.

The first indication of a stimulatory effect was noted during a determination of the pH optimum of the trypsin-like amidase activity in *P. gingivalis*. These enzymes require $Ca^{++}$ for stability as well as reducing agents for the detection of amidase and proteinase activity[1]. Using N-benzoyl-L-arginine-p-nitroanilide (BAPNA) it was noted that neutral pH buffers containing glycinc (50 mM) significantly stimulated the amidase activity (up to five-fold) in crude extracts obtained by solubilisation with 0.05M Tris-HCi, 0.2 NaCl, 10 mM $CaCl_2$, Ph 7.5, provided that reducing agents (5 mM) were present during amidase assays. Later it was found that glycyl-glycine was even more stimulatory than free glycine, and this was utilized in all buffers during an analysis of the pH optimum for BAPNA activity in crude extracts (FIG. 1).

In the absence of glycyl-glycine the pH optimum was found to be broad with only a modest increase in activity between pH 6.0 and 9.0. However, in the presence of this stimulatory agent substantial sharpening of the pH profile for amidase activity was observed, with the optimum being between pH 7.3 and 8.0.

In FIG. 1, the effect of glycyl-glycine on the pH-dependent hydrolysis of BAPNA by proteinases present in *P. gingivalis* crude extracts is displayed. Samples were incubated in either 0.2M Bis-Tris-HCl buffer (pH 6.0–7.2) or 0.2M Tris-HCl buffer (pH 7.4–9.0), both containing 5 mM $CaCl_2$, 5 mM cysteine, in the absence (closed circles) or presence (open circles) of 50 mM glycyl-glycine and assayed for amidase activity using 1 mM BAPNA.

[1] Both crude extracts and purified proteinases lost activity in the absence of $Ca^{++}$, which could not be recovered upon readdition of this ion. However, samples stored in the presence of 5 mM $C^{++}$ remained stable for several days. Since no activation of enzyme activity was noted when $Ca^{++}$ was added to crude extracts, it appears that this ion prevents autolytic inactivation of proteinase activity.

Testing of both individual amino acids (FIG. 2A) and dipeptides (FIG. 2B) (50 mM) indicated that glycine containing compounds, particularly glycylamide and glycyl-glycine, were by far the most stimulatory for amidase activity, other amino acids showing either no effect or only a very slight stimulation. Dipeptides with structures equivalent to or related to artificial sweeteners were found to have variable activities on *P. gingivalis* extracts, with both aspartyl-phenylalanine methyl ester (aspartane) and aspartyl-phenylalanine amide increasing amidase activity over two-fold. In contrast, the hydrolysis product of aspartane, aspartyl-phenylalanine, had essentially no effect. However, at concentrations equivalent to that found in diet soft drinks (2 mM) stimulation was barely detectable.

Figure 2A:
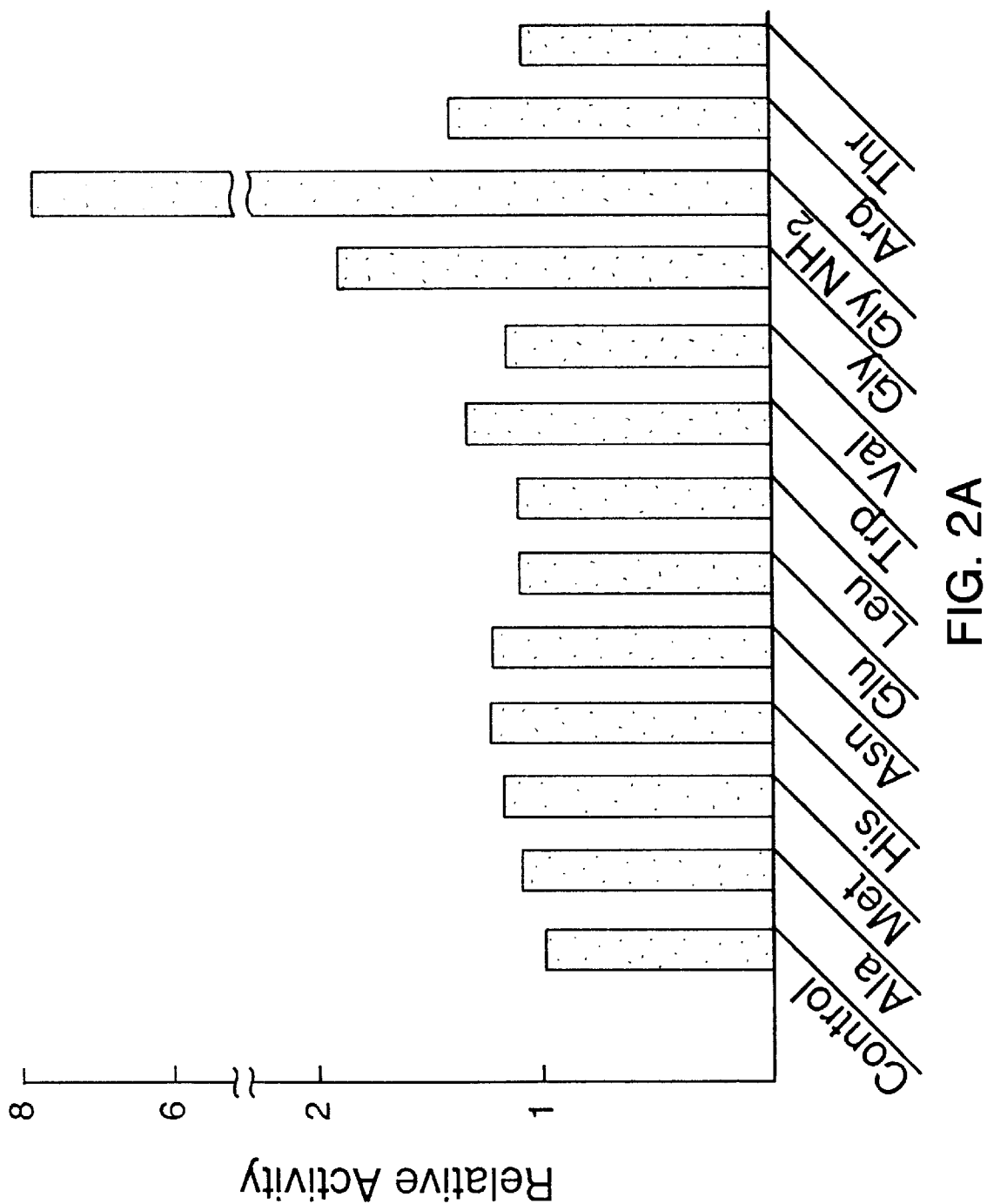
FIG. 2a is a diagram showing relative stimulatory (activating) effect of various amino acids and an amide.
Figure 2B:
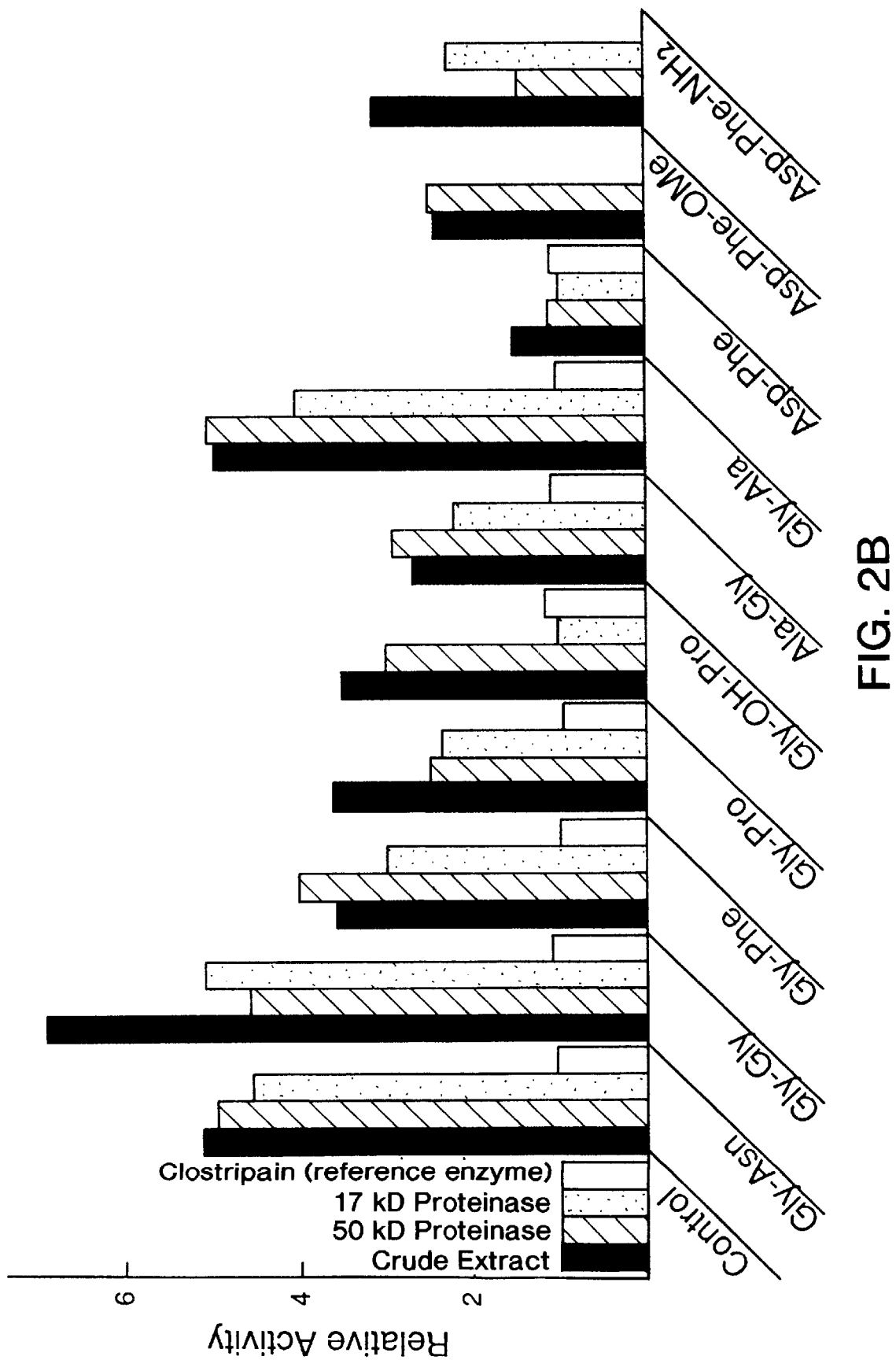
FIG. 2b is a diagram showing relative stimulatory (activating) effect of various peptides and derivatives thereof.

In FIGS. 2A and 2B, the effect of the amino acids Ala, Met, His, Asn, Glu, Leu, Trp, Val, Gly, Arg, and Thr, the dipeptides Gly-Asn, Gly-Gly, Gly-Phe, Gly-Pro, Ala-Gly, Gly-Ala, Asp-Phe, and Gly-$NH_2$ and Asp-Phe-$NH_2$.

Testing of two purified proteinases (apparent molecular weights of 17 kD and 50 kD) isolated from *P. gingivalis* extracts and/or culture media by conventional gel filtration followed by either ion-exchange chromatography (17 kD) or affinity chromatography on benzamidine-sepharose 50 kD)[2] indicated that each was stimulated in a similar manner to that found with crude extracts (FIG. 2B). However, this effect was not quite as large as that found with crude extracts (five-fold for each purified enzyme versus eight-fold with extracts). Glycine and glycylamide also stimulated the amidase activity of each enzyme (data not shown). Significantly, the bacterial proteinase clostripain (Sigma) obtained from the anaerobe *Clostridium histolyticum* was totally unaffected by any of the amino acids or dipeptides tested, despite the fact that it also requires both $Ca^{++}$ and a reducing agent for maximum activity.

[2] The 17 kD proteinase was isolated from one of four proteinase-containing peaks obtained after gel filtration on Sephadex G-100. After ethanol fractionation the enzyme was purified by ion-exchange chromatography on DEAE-cellulose followed by FPLC using a Mono-Q column. The 50 kD proteinase was also isolated from one of the gel filtration peaks and purified by affinity chromatography on benzamidine-sepharose. The bound enzyme was isolated by elution with 0.01N HCl and immediately neutralized with 1.0M Tris-HCl buffer, pH 8.0. All neutral pH buffers used in the isolation of each enzyme contained 5 mM $Ca_{++}$.

Testing of both crude extracts and purified enzymes for proteolytic activity, using azocasein and azocoll as substrates, indicated that this activity was also stimulated by glycine-containing compounds. Increases in activity ranged from 1.7-fold (glycyl-hydroxyproline) to 4.4-fold (glycyl-glycine) over controls for purified enzymes. Crude extracts were less affected, presumably because of the presence of some proteolytic activity not susceptible to stimulation.

Figure 3A:
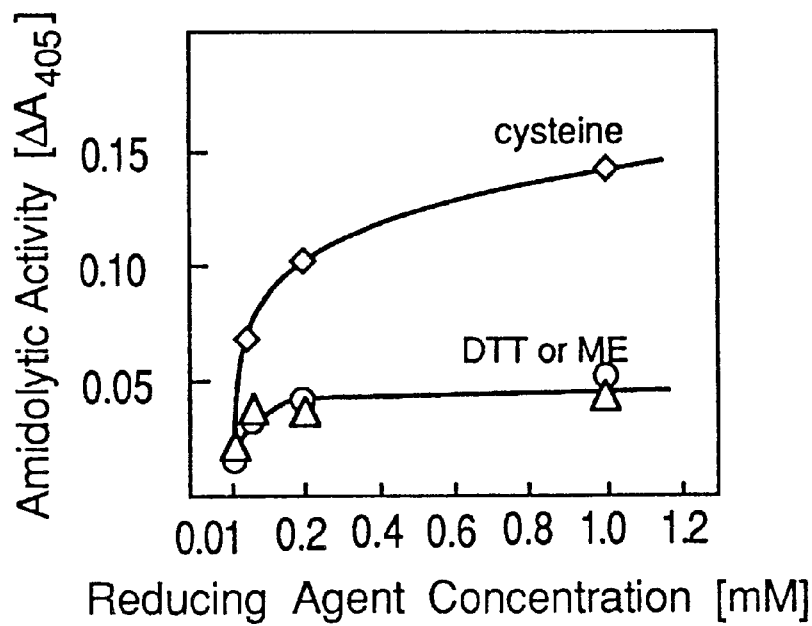
FIG. 3a is a diagram showing the effect of the reducing agents cysteine, DTT and ME on the amidolytic activity of *P. gingivalis* proteinases.
Figure 3B:
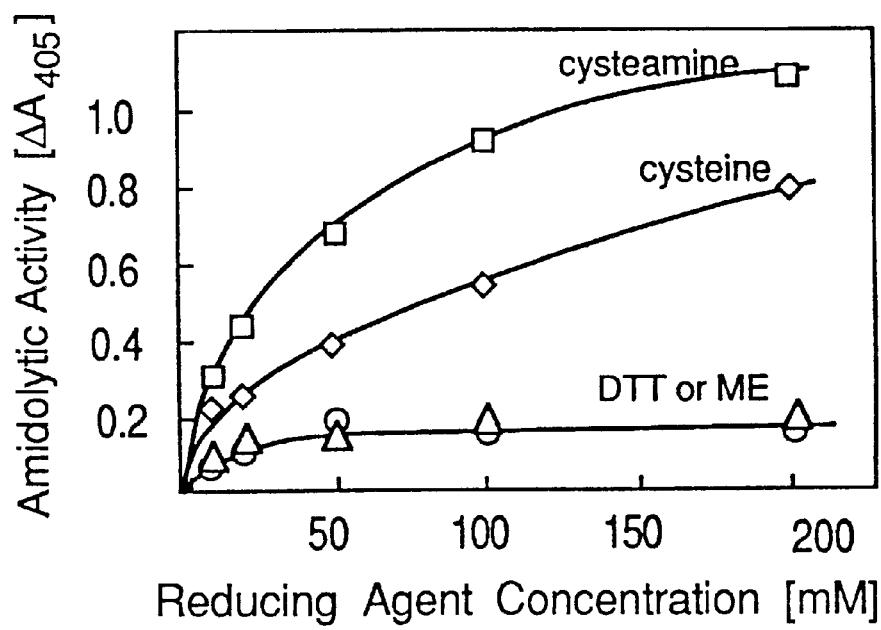
FIG. 3b is a diagram showing the effect of reducing agents cysteamine, cysteine, DTT or ME on the amidolytic activity of *P. gingivalis* proteinases.
Figure 3C:
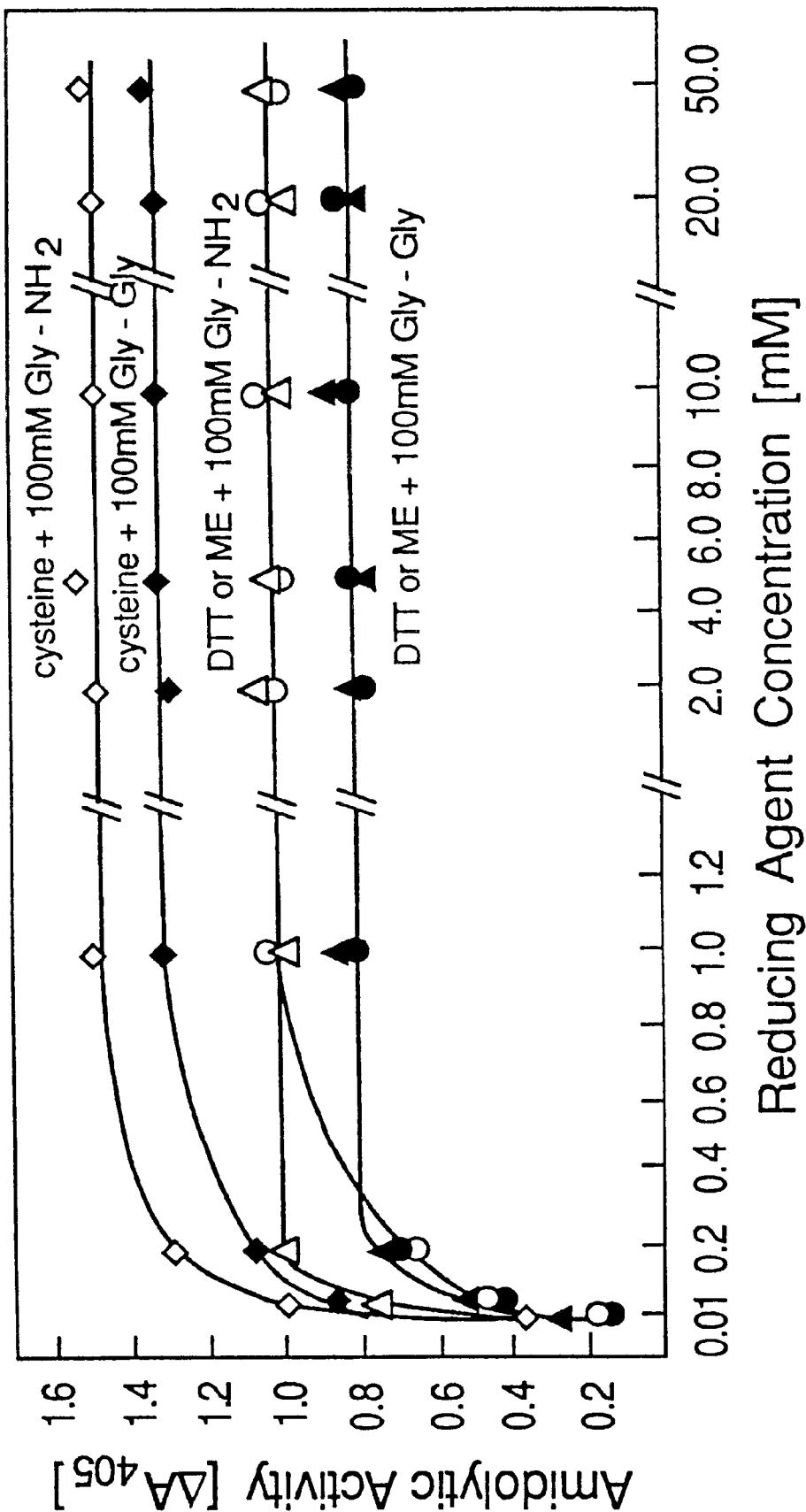
FIG. 3c shows the effect of glycine-containing compounds and/or reducing agents on the amidolytic activity of *P. gingivalis* proteinases.

The effect of cysteine was of some significance since other reducing agents such as 2-mercaptoethanol and dithiothreitol were not nearly as effective in stimulating amidase activity in the absence of glycine containing compounds (FIGS. 3A and 3B). In the presence of glycyl-glycine and glycylamide maximum enhancement of amidolytic activity could readily be attained at low reducing agent concentrations (0.5 mM) (FIG. 3C). However, marked differences in the degree of activation in the presence of individual thiol-containing compounds was also noted with cysteine giving a much greater stimulatory effect than that of either 2-mercaptoethanol or dithiothreitol. This suggested that cysteine, itself, might be acting both as a reducing agent and a stimulating agent. To test this hypothesis a number of thiol-containing compounds were utilized in an assay system containing no other sources of either reducing or stimulating agents. In particular, the effect of cysteamine was studied since the carboxyl group at glycine appeared to reduce stimulation (glycine versus glycinamide). As expected (FIG. 3B), cysteamine could best fulfill the dual role required for *P. gingivalis* amidase and proteinase activity.

Determination whether *P. gingivalis* is present in the subgingival space is currently usually performed by microbiological cultivation techniques. These methods are expensive and require about two weeks to give a therapist the result. As shown in Table 1, however, patient samples collected from discrete *periodontitis* sites show a strong enhancement of trypsin-like amidase activity in the presence of glycyl-glycine only in individuals who are also infected with *P. gingivalis*. Since there is virtually no activity against the substrate BAPNA in crevicular fluids in the absence of glycine-containing compounds, the use of these stimulating agents makes it possible for the first time to quickly and directly assay for the presence of *P. gingivalis* in periodontal sites.

These results indicate that proteins highly enriched in glycine, such as collagen, could serve as sources of stimulatory agents to increase the proteolytic activity of enzymes secreted by and found in *P. gingivalis* Since it has previously been reported that *P. gingivalis* contains significant collagenolytic activity apparently unrelated to the trypsin-like amidase or proteinase activity, it is possible that this organism has adapted to use collagen not only as a source of nutrients in the dento-gingival crevice but also for the production of glycine-containing peptides to increase the rate of proteolysis of both this and other proteins.

It appears that stimulation of the proteolytic activity in an enzyme by glycine-containing compound or by amino acids and dipeptides, in general, was not previously reported. While it has been known for sometime that specific peptides can stimulate conformational changes in trypsinogen to approximate that of trypsin, such a reaction appears to involve a very different type of interaction since there is no enhancement of the trace activity associated with this zymogen after peptide binding. In the case of *P. gingivalis*, however, both amidase and proteinase activity can readily be measured in either crude extracts or purified enzymes in the absence of glycine-containing compounds, so that the effect given by the addition of glycyl-glycine or glycylamide involves the stimulation rather than the generation of activity. While the mechanism by which this occurs is as yet unknown the phenomenon, itself, may be of significant value in the ultimate development of inhibitors for the reduction of proteinase activity and, thereby, that of periodontitis-related tissue destruction.

Characterization of peptide and amino acids derivatives effect on proteolytic enzymes.

A) Gly-Gly or Gly-amide does not have any effect on activity of:
1. Scrine proteinases (trypsin, chymotrypsin and elastase and subtylisin)
2. Metalloproteinases (thermolysin, S.aurcus metalloproteinase)
3. Cysteine proteinases (clostripain, papain and cathepsin B)
4. Effect of Gly-Gly (50mM) and glycylamide (100 mM) on amidolytic activity of crude extract of human liver (rich source of cathepsins, amino- and carboxy-peptidases), pancreas (abundant in peptidases and proteinases), leucocytes (HLE, cathepsin G and other cysteine cathepsins, mctalloproteinases) and rabbit testicles (acrosin and cathepsins).

All extracts show amidolytic activity on Benzoyl-Arg-p-nitroanilide (BAPNA) and Bz-Arg-naphtylamide (BANA)

| | | |
|---|---|---|
| 1. | P. gingivalis | Bg 100 |
| 2. | Prevotella intermedius* | Bi 37 |
| 3 | Prevotella intermedius* | Bi 30 |
| 4. | A. actinomycetemcomitans | Y4 |
| 5. | A. actinomycetemcomitans | Aa 1032 |
| 6. | Wolinella curve | |
| 7. | Wolinella recta | |
| 8. | Wolinella recta | W 390 |
| 9. | Fusobacterium nucleatum | Fus 9126 |
| 10. | F. peridonticum | Fus 907 |

*(Formerly Bacteroides intermedius)

100 mg of lyophilized bacterial strains was crushed in glass-glass homogenizer in 1 ml of buffer. Insoluble particles were centrifuged for 5 min at 13,000×G and in supernatant amidolytic activity was determined.

Activity: $A_{405}/1\ \mu l/60$ min.

| | A | B | C | D | B/A | C/A | D/A | C/B | D/B |
|---|---|---|---|---|---|---|---|---|---|
| 1. | 0.0936 | 0.5793 | 3.4320 | 4.9320 | 6.1 | 36.7 | 52.7 | 5.9 | 8.5 |
| 2. | <0.001 | <0.001 | <0.001 | <0.001 | — | — | — | — | — |
| 3. | <0.001 | <0.001 | <0.001 | <0.001 | — | — | — | — | — |
| 4. | 0 | 0 | 0 | 0 | — | — | — | — | — |
| 5. | 0 | 0 | 0 | 0 | — | — | — | — | — |
| 6. | <0.001 | <0.001 | <0.001 | <0.001 | — | — | — | — | — |
| 7. | <0.001 | <0.001 | <0.001 | <0.001 | — | — | — | — | — |
| 8. | <0.001 | <0.001 | <0.001 | <0.001 | — | — | — | — | — |
| 9. | 0.0015 | 0.0015 | 0.0026 | 0.0032 | 1.0 | 1.7 | 2.1 | 1.7 | 2.1 |
| 10. | 0.0016 | 0.0026 | 0.0048 | 0.0060 | 1.6 | 3.0 | 3.7 | 1.8 | 2.3 |
| ratio | | | | | | | | | |
| 1/10 | 62 | 223 | 715 | 822 | | | | | |

A. 0.2 M Tris-HCl, 5 mM $CaCl_2$, pH 7.5
B. 0.2 M Tris-HCl, 5 mM $CaCl_2$, 5 mM Cys, Ph 7.5
C. 0.2 M Tris-HCl, 5 mM $CaCl_2$, 5 mM Cys, 50 mM Gly-Gly, pH 7.5
D. 0.2 M Tris-HCl, 5 mM $CaCl_2$, 5 mM Cys, 100 mM Gly-amide, pH 7.5

(pancreas>liver>testicles>leucocytes) but in none of the extracts tested amidolytic activity was stimulated by Gly-Gly or glycylamide. On the contrary, the trypsin-like amidolytic activity was inhibited by these compounds in testicles, liver and leucocyte extracts.

Thus the activation effect of Gly-Gly and Gly-amide is group specific and limited only to bacterial enzymes. BAPNA as a substrate B) Effect of glycylamide on human tryptase (mast cell proteinase), amidolytic activity.

Glycylamide, at low concentrations and in the absence of heparin (present in tissues as a physiological tryptase activator) activates tryptase but has no effect on enzyme activity at concentration higher than 100 mM. Moreover, in the presence of heparin glycylamide acts as tryptase inhibitor.

Thus, using Gly-amide at concentration of 100 mM as a P. gingivalis proteinase stimulator is very useful because it eliminates tryptase activity (tryptase was found in crevicular fluid) which might interfere with the specificity of P. gingivalis detection in clinical samples.

C) Trypsin-like activity in different subgingival strains of bacteria.

The following bacterial strains were used for determination of amidolytic activity on BAPNA and BANA as a substrate.

1. Among so far tested bacteria only Fusobacterium shows some trypsin-like amidolytic activity but this activity is much lower than the one expressed by P. gingivalis (see ratio 1/10).
2. Difference in activity between these two strains is enhanced in the presence either Gly-Gly or Gly-amide due to weaker stimulatory effect expressed by these compounds on amidolytic activity of Fusobacterium proteinases than on P. gingivalis proteinases (see activation factor).
3. Due to both above effects proteinase(s) released by Fusobacterium should not interfere with test specificity for detecting of P. gingivalis which is based on Gly-Gly or Gly-amide amidolytic activity stimulation.

D) Either in P. gingivalis extract or in clinical samples of gingival crevicular fluid from periodontitis sites infected with P. gingivalis Gly-Gly stimulated BAPNA, hydrolysing activity is resistant for inhibition by
1. Di-fluorophosphate (DFP) and 3,4-dichloroisocumarin (DIC)
2. Cystatin C Thus, BAPNA hydrolysing activity in crevicular fluid is not due to host serine proteinases (should be inhibited by either DFP or DIC) or cysteine proteinases as cathopsine B, H and L which are very strongly inhibited by cystatin C. Moreover, lysosomal cysteine proteinases are very unstable at pH above 7. Also metalloproteinases can be excluded because they do not degrade p-nitroanilide substrates.

Laboratory approach to measure trypsin-like amidolytic activity of P. gingivalis proteinases.

Buffers:
A) 0.2 M Tris-HCl, 5 mM $CaCl_2$, pH 7.5
B) 0.2 M Tris-HCl, 5 mM $CaCl_2$, 5 mM Cys, pH 7.5
C) 0.2 M Tris-HCl, 5 mM $CaCl_2$, 5 mM Cys, 50 mM Gly-Gly, pH 7.5

890 µl of buffer A, B or C
+
100 µl suitably diluted sample
+
10 µl of 0.1M BAPNA in DMSO incubation at room temp.

After assay mixture turned yellow reaction is terminated by addition of 50 µl glacial acetic acid and the absorbance at 405 nm ($A_{405}$) is measured. (The absorbance maximum for nitroanilide is 405–410 nm.) Activity is then expressed as the increase of $A_{405}$ during 60 min, calculated for 1 µl of undiluted sample.

P. gingivalis proteolytic enzymes detection in clinical samples.

The assay was performed in BSA (bovine serum albumin)—coated flat bottom wells of microtitration plates. 140 µl of buffer A or C was placed into the well
+
10 µl of gingival crevicular fluid sample (150 µl of buffer in which 2–3 paper points were placed and this was frozen.)
+
50 µl of BAPNA (0.4 mM) diluted in the buffer—final concentration=0.1 mM The wells were incubated at 37° C. and $A_{405}$ was measured after 3–12 h.

A simplified version of clinical assay kit to detect P. gingivalis Presence in gingival crevicular fluid samples.

The samples from the same periodontitis site are taken on two paper points. One paper point is placed into a well A containing 200 µl 0.2 M Tris-Hcl, 5 mM $CaCl_2$, 1.0 mM cysteine 0.1 mM BAPNA, pH 7.5, and the second one into the well B containing 200 µl of above buffer supplemented with 100 mM Gly-amide. Development of yellow color in both wells can be monitored by eye or $A_{405}$ can be measured over a time of incubation at room temperature.

The result of the test is positive for P. gingivalis if yellow color developed faster in the well B.

Final test to detect P. gingivalis in clinical samples.

Right now use of histochemical staining substrates (Bz-Arg-β-naphtylamide and B2-Arg-4-methoxy-β-naphtylamide) to determine P. gingivalis proteinases in clinical samples is under investigation. The goal is to prepare a simple test to specifically detect the presence of P. gingivalis just by dipping a strip into a buffer (0.2 M Tris-$HCl_1$, 5 mM $CaCl_2$, 5 mM cysteine, pH 7.5) in which paper points containing crevicular fluid samples were placed.

Strip A will have the pad impregnated with a suitable histochemical substrate and diazonium salt.

On Strip B the pad will be saturated with substrate, diazonium salt and Gly-amide.

The test will be positive for P. gingivalis if visible color develops only on strip B or if stronger color develops on strip B than on strip A.

TABLE 1

TRYPSIN-LIKE AMIDOLYTIC ACTIVITY IN CLINICAL SAMPLES COLLECTED FROM DISCRETE PERIODONTITIS SITES
Bacteria species present Activity units in periodontitis site

| Sample No. | A.a | B.g | B.i | Gly—Gly | Buffer only | Stimulation factor |
|---|---|---|---|---|---|---|
| 341. | – | – | – | 0 | 0 | – |
| 357. | – | – | – | 0 | 0 | – |
| 507. | – | – | – | 0 | 0 | – |
| 174. | – | – | – | 0.010 | 0.012 | 0.9 |
| 492. | +++ | – | – | 0 | 0 | – |
| 142. | ++ | – | – | 0 | 0 | – |
| 207. | ++ | – | – | 0 | 0 | – |
| 163. | – | – | ++ | 0.017 | 0.008 | 2.0 |
| 465. | – | – | ++ | 0 | 0 | – |
| 345. | – | – | + | 0 | 0 | – |
| 6. | – | – | + | 0.009 | 0.011 | 0.9 |
| 8. | – | – | + | 0.028 | 0.027 | 1.0 |
| 62. | + | – | + | 0 | 0 | – |
| 315. | + | – | ++ | 0 | 0 | – |
| 323. | + | – | ++ | 0.010 | 0.016 | 0.6 |
| 26. | ++ | – | + | 0 | 0 | – |
| 187. | ++ | – | + | 0.023 | 0.023 | 1.0 |
| 15. | – | + | + | 0.467 | 0.014 | 32.0 |
| 16. | – | ++ | + | 0.413 | 0.012 | 33.0 |
| 19. | – | ++ | + | 0.947 | 0.029 | 33.0 |
| 20. | – | ++ | + | 0.488 | 0.010 | 47.0 |
| 50. | – | ++ | + | 0.860 | 0.021 | 42.0 |
| 53. | – | ++ | ++ | 1.370 | 0.033 | 42.0 |
| 56. | – | ++ | + | 1.213 | 0.047 | 26.0 |
| 126. | + | + | + | 0.940 | 0.057 | 16.0 |
| 22. | – | + | – | 0.152 | 0.044 | 35.0 |
| 122. | – | +++ | – | 2.540 | 0.050 | 50.0 |
| 179. | – | +++ | – | 3.405 | 0.06 | 57.0 |

Samples of crevicular fluid from periodontitis sites were collected with 2–3 paper points which were placed into 150 µl of buffer and immediately frozen at −80° C. Bacterial species present in samples were determined using standard microbiological methods. The activity assay was performed in BSA coated flat bottom microtliter plates in total volume of 200 µl of 0.2 M Tris-HCl, 5 mM $CaCl_2$, pH 7.5 supplemented or not with 5 mM cysteine and 50 mM Gly-Gly using 0.1 mM (final concentration) of BAPNA as a substrate. The $A_{405}$ was measured 3–4 times during 24 hrs incubation at 37° C. using Eliza reader and activity units were calculated.

One unit of activity is equal to the amount of enzyme which hydrolyses 1 nmol of BAPNA during 1 h of incubation.

"–" no bacteria were detected
"+" less than 25% of bacterial flora
"++" from 25 to 50% of bacterial flora
"+++" more than 50% of bacterial flora FIG. 1. Effect of glycyl-glycine on the pH-dependent hydrolysis of BAPNA by proteinases present in P. gingivalis crude extracts. Samples were incubated in either 0.2 M Bis-Tris-HCl buffer (pH 6.0–7.2) or 0.2M Tris-HCl buffer (pH 7.4–9.0), both containing 5 mM $CaCl_2$, 5 mM cysteine, in the absence (0----0) or presence (0----0) of 50 mM glycyl-glycine and assayed for amidase activity using 1 mM BAPNA.

FIG. 2A and 2B. Effect of amino acids and dipeptides on the amidase activity of crude extracts and purified proteinases from P. gingivalis and clostripain from Clostridium histolyticum. Samples were incubated in a buffer system composed of 0.2M Tris-HCl, 5 mM CaC$_2$, 5 mM cysteine, pH 7.4 in the presence of 50 mM concentrations of each compound tested and then tested against BAPNA (1 mM). Controls contained only buffer and the activity generated given an activity value of 1.0. Aspartane (Asp-Phe-OMe) was not tested against the 17 kD protcinasc. (FIG. 2A), effect of amino acids and glycylamide; (FIG. 2B), effect of glycine-containing dipeptides and aspartane-related compounds.

FIG. 3. Effect of glycine-containing compounds and/or reducing agents on the amidolytic activity of *P. gingivalis* proteinases. Samples were incubated in 0.2M Tris-HCl, 5 mM CaCl$_2$, pH 7.5, in the presence of either low (A) or high (B) concentrations of reducing agents. Assays for residual amidolytic activity using BAPNA (1 mM) were then measured in the absence (FIG. 3A and FIG. 3B) or presence (FIG. 3C) of glycine-containing compounds. (FIG. 3A and FIG. 3B), (◇), cysteine; (Δ), 2-mercaptoethanol; (○), dithiothreitol; (□), cysteamine. (FIG. 3C), incubations made in the presence of various reducing agents plus either glycinamide (1200 mM) (open symbols) or glycyl-glycine (closed symbols). (◇, ♦), cysteine; (Δ, ▲), 2-mercaptoethanol; (○, ●), dithiothreitol.

I claim:

1. A method for detecting *Porphyromonas gingivalis* in a sample comprising the steps of:
    reacting a sample suspected of containing *Porphyromonas gingivalis* with a composition to form a reaction mixture, said composition comprising:
        a substrate for a trypsin-like amidase enzyme;
        a marker system which generates a signal correlated to lysis of said substrate; and
        an enhancer selected from the group consisting of Gly-NH$_2$, Gly-Asn, Gly-Gly, Gly-Phe, Gly-Pro, Gly-OH-Pro, Ala-Gly, and Gly-Ala; and
    analyzing the reaction mixture for a signal generated by said marker system, which signal correlates to the presence of *Porphyromonas gingivalis* in said sample.

2. The method of claim 1, wherein the enhancer is Gly-NH$_2$.

3. The method of claim 1, wherein the enhancer is Gly-Gly.

4. The method of claim 1, wherein the enhancer is Gly-Asn.

5. The method of claim 1, wherein the enhancer is Gly-Phe.

6. The method of claim 1, wherein the enhancer is Gly-Pro.

7. The method of claim 1, wherein the enhancer is Gly-OH-Pro.

8. The method of claim 1, wherein the enhancer is Ala-Gly.

9. The method of claim 1, wherein the enhancer is Gly-Ala.

10. The method of claim 1, wherein said composition further comprises at least one reducing agent.

11. The method of claim 10, wherein said reducing agent is selected from the group consisting of cysteamine, 2-mercaptoethanol, cysteine, and dithiothreitol.

12. The method of claim 11, wherein said reducing agent is cysteamine.

13. The method of claim 1, wherein said enzyme is selected from the group consisting of peptidase and amidase.

14. The method of claim 1, wherein said substrate is a peptide, amide, or derivative thereof.

15. The method of claim 1, wherein said substrate is a peptide to which a chromogenic or flourogenic group is attached.

16. The method of claim 1, wherein said substrate is N-benzyl-L-arginine-p-nitroanilide (BAPNA) or benzoyl-arginine-beta-napthylamide (BANA).

17. A method for detecting *Porphyromonas gingivalis* in a sample comprising the steps of:
    reacting a sample suspected of containing *Porphyromonas gingivalis* with a composition to form a reaction mixture, said composition comprising:
        a substrate which for at least one enzyme of *Porphyromonas gingivalis*;
        a marker system which generates a signal correlated to lysis of said substrate; and
        an enhancer of the enzyme, wherein the enhancer is selected from the group consisting of: Gly-NH$_2$, Gly-Asn, Gly-Gly, Gly-Phe, Gly-Pro, Gly-OH-Pro, Ala-Gly, and Gly-Ala; and
    analyzing the reaction mixture for a signal generated by said marker system, which signal correlates to the presence of *Porphyromonas gingivalis* in said sample.

18. A kit for the detection of *Porphyromonas gingivalis* comprising:
    a sampling means for collecting a sample from a site of possible *Porphyromonas gingivalis* contamination; and
    a composition for reacting with the sample to diagnose *Porphyromonas gingivalis*, said composition comprising:
        a substrate for a trypsin-like amidase enzyme;
        a marker system which generates a signal correlated to lysis of said substrate; and
        an enhancer selected from the group consisting of Gly-NH$_2$, Gly-Asn, Gly-Gly, Gly-Phe, Gly-Pro, Gly-OH-Pro, Ala-Gly and Gly-Ala.

19. The kit of claim 18, wherein said enhancer is Gly-NH$_2$.

20. The kit of claim 18, wherein said enhancer is Gly-Gly.

21. The kit of claim 18, wherein said composition comprises at least one reducing agent.

22. The kit of claim 21, wherein the reducing agent is cysteamine.

23. The kit of claim 21, wherein said reducing agent is selected from the group consisting of cysteamine, 2-mercaptoethanol, cysteine and dithiothreitol.

24. The kit of claim 18, wherein the enhancer is Gly-Asn.

25. The kit of claim 18, wherein the enhancer is Gly-Phe.

26. The kit of claim 18, wherein the enhancer is Gly-Pro.

27. The kit of claim 18, wherein the enhancer is Gly-OH-Pro.

28. The kit of claim 18, wherein the enhancer is Ala-Gly.

29. The kit of claim 18, wherein the enhancer is Gly-Ala.

30. The kit of claim 18, wherein said substrate is a peptide, amide or derivative thereof.

31. The kit of claim 18, wherein said substrate is a peptide to which a chromogenic or flourogenic group is attached.

32. The kit of claim 18, wherein said substrate is N-benzyl-L-arginine-p-nitroanilide (BAPNA) or benzoyl-arginine-beta-napthylamide (BANA).

* * * * *